US008367635B2

(12) United States Patent
McGrath

(10) Patent No.: US 8,367,635 B2
(45) Date of Patent: Feb. 5, 2013

(54) ANTIMICROBIAL SUCRALFATE PASTE METHODS AND COMPOSITIONS

(76) Inventor: Patrick D. McGrath, Gurnee, IL (US)

( * ) Notice: Subject to any disclaimer, the term of this patent is extended or adjusted under 35 U.S.C. 154(b) by 0 days.

(21) Appl. No.: 13/049,488

(22) Filed: Mar. 16, 2011

(65) Prior Publication Data

US 2012/0064139 A1    Mar. 15, 2012

Related U.S. Application Data

(63) Continuation of application No. PCT/US2009/056374, filed on Sep. 9, 2009.

(60) Provisional application No. 61/097,674, filed on Sep. 17, 2008.

(51) Int. Cl.
*A61K 31/737*    (2006.01)
*A61K 9/00*    (2006.01)

(52) U.S. Cl. .................................. 514/53; 536/18.5

(58) Field of Classification Search ............... 514/53; 526/18.5
See application file for complete search history.

(56) References Cited

U.S. PATENT DOCUMENTS

| | | | |
|---|---|---|---|
| 3,432,489 A | 3/1969 | Nitta et al. | |
| 4,668,665 A | 5/1987 | Ishihara et al. | |
| 5,196,405 A | 3/1993 | Packman | |
| 5,321,013 A * | 6/1994 | Zagnoli et al. | 514/53 |
| 5,358,936 A | 10/1994 | Gordon et al. | |
| 5,968,906 A * | 10/1999 | Kashimura et al. | 514/23 |
| 6,391,860 B1 | 5/2002 | McGrath | |
| 7,128,903 B2 | 10/2006 | Burstein | |
| 2002/0197259 A1 | 12/2002 | Kodama et al. | |
| 2004/0157766 A1 | 8/2004 | Embil et al. | |
| 2006/0015083 A1 | 1/2006 | Munro et al. | |
| 2007/0036858 A1 | 2/2007 | Schneider | |

FOREIGN PATENT DOCUMENTS

WO    WO 89/05645    6/1989

OTHER PUBLICATIONS

S. Rossi et al., "Rheological Study of Sucralfate Humid Gel: a Contribution to the Comprehension of its Stability Properties," *Eur. J. Pharm. Biopharm.*, vol. 38, No. 2, 78-81, 1992.
D. Vaira et al., "Gastric retention of sucralfate gel and suspension in upper gastrointestinal diseases," *Aliment Pharmacol. Ther.*, vol. 7, 531-535, 1993.
M. Guslandi et al., "Effect of a Gel Formulation of Sucralfate on Gastric Microcirculation," *J. Int'l. Med. Res.*, 21: 47-50, 1993.
A. P. West et al., "Antibacterial activity of sucralfate against *Escherichia Coli, Staphylococcus aureus* and *Pseudomonas aeruginosa* in batch and continuous culture," *Eur. J. Clin. Microbiol. Infect. Dis.*, vol. 12, No. 11, 1993 (Abstract only).
D. Bergmans et al., "In vitro antibacterial activity of sucralfate," *Eur. J. Clin. Microbiol. Infect. Dis.*, vol. 13, No. 7, 1994 (Abstract only).
S. G. L. Bragman et al., "Activity of sucralfate (sucrose octasulphate), an anti-ulcer agent, against opportunistic Gram-negative bacilli," *J. Antimicrob. Chemother.*, vol. 36, Issue 4, 703-706, 1995 (Abstract only).
BL. Slomiany et al., "Sucralfate affects the susceptibility of *Helicobacter pylori* to antimicrobial agents," *Scand. J. Gastroenterol. Supp.*, 210, 82-84, 1995 (Abstract only).
M. Miglioli et al., "Prevention with Sucralfate Gel of NSAID-Induced Gastroduodenal Damage in Arthritic Patients," *Am. J. Gastroenterol.*, vol. 91, No. 11, 2367-2371, 1996.
PCT International Search Report and the Written Opinion, Oct. 2009.

* cited by examiner

*Primary Examiner* — Michael G Hartley
*Assistant Examiner* — Nabila Ebrahim
(74) *Attorney, Agent, or Firm* — Haynes and Boone, LLP

(57) ABSTRACT

Methods for the prevention and treatment of infection, preferably antibiotic resistant wound infection, using a paste formed by the reaction of sucralfate with an acid component are provided. Methods of preparing stable sucralfate compositions are disclosed. Compositions of and products containing the sucralfate paste are also described.

5 Claims, No Drawings

ANTIMICROBIAL SUCRALFATE PASTE METHODS AND COMPOSITIONS

CROSS REFERENCE TO RELATED APPLICATIONS

This is a continuation application of Application No. PCT/US2009/056374 filed Sep. 9, 2009, which claims priority to U.S. Provisional Application No. 61/097,674 filed on Sep. 17, 2008, the contents of each which is hereby incorporated herein in its entirety by express reference thereto.

TECHNICAL FIELD

The present invention relates generally to methods of prevention and treatment of infections, preferably antibiotic resistant wound infections, by applying a sucralfate paste formed by reaction of sucralfate with an acid component. The invention further relates to compositions of sucralfate paste and methods for producing the same.

BACKGROUND OF THE INVENTION

Sucralfate is a complex of sucrose octasulfate and aluminum hydroxide. Sucralfate is insoluble in water but dissolves in hydrochloric acid, releasing sucrose sulfate and free aluminum. Prior to complete dissolution, sucralfate reacted with hydrochloric acid forms an amorphous paste for therapeutic use in connection with ulcers. The mechanism of action of sucralfate is incompletely understood, but includes the protection of ulcerated tissue by physical coverage of the wound base by this amorphous paste.

The use of sucralfate for the treatment of ulcers is known in the art. For example, in his letter to the editor in American Family Physician, January 1995, B. C. Demoss, M.D. contemplated the use of sucralfate tables (Carafate®) in treating aphthous ulcers. Sucralfate gel suspensions have also been employed as an antiulcerative drug. See S. Rossi et al., "Rheological Study of Sucralfate Humid Gel: a Contribution to the Comprehension of its Stability Properties," Eur. J. Pharm. Biopharm. 1992:38:78-81.

The use of sucralfate gels as an ulcer healing drug has been detailed in other journals as well. See M. Guslandi et al., "Effect of a Gel Formulation of Sucralfate on Gastric Microcirculation," J. Int'l Med. Res. 1993; 21: 47-50; see also M. Miglioli, "Prevention with Sucralfate Gel of NSAID-Induced Gastroduodenal Damage in Arthritic Patients," Am. J. Gastroenterology, Vol. 91, No. 11, 1996; D. Vaira, "Gastric Retention of Sucralfate Gel and Suspension in Upper Gastrointestinal Diseases," Ailment Pharmacol. Ther. 1993; 7:531-535.

U.S. Pat. No. 3,432,489 to Yoshihiro et al. discloses a disaccharide polysulfate-aluminum compound for use as a peptic ulcer inhibitor.

U.S. Pat. No. 6,391,860 to McGrath describes methods for preparation and use of a paste of sucralfate prepared by the reaction between sucralfate and hydrochloric acid prior to dosing under controlled conditions that limit the reaction to an incomplete stage. The formation of a paste by the controlled and limited reaction of sucralfate tablets with 1.0N HCl to form a biologically active paste prior to dosing creates the opportunity to use sucralfate as a physical wound dressing in conditions other than duodenal ulcer.

U.S. Pat. No. 7,128,903 to Burstein describes the use of acids, such as trichloroacetic acid, hydrochloric acid, trichloroacetic acid, and formic acid to treat skin or mucous membrane lesions.

In addition, the antibacterial effect of sucralfate was studied in A. P. West et al., "Antibacterial activity of sucralfate in *Escherichia coli*, *Staphylococcus aureus*, and *Pseudomonas aeruginosa* in batch and continuous culture," Eur. J. Clin. Microbiol. Infect. Dis. 12, 869-871 (1993). Inhibitory and bactericidal activity of sucralfate in suspension was reported in S. G. L. Bragman et al., "Activity of sucralfate (sucrose octasulphate), an anti-ulcer agent, against opportunistic Gram-negative bacilli," J. Antimicrob. Chemother., (1995) 36, 703-706 of sucralfate in suspension. The effect of sucralfate on the growth of certain bacteria was tested in D. Bergmans et al., "In vitro antibacterial activity of sucralfate," Eur. J. Clin. Microbiol. Infec. Dis., 1994 July; 13 (7) 615-20.

As antibiotics have been used more and more to treat diseases caused by microorganisms, many of these microorganisms have become resistant to, or untreatable by, the overused drug. One well known example of such a microorganism is methicillin-resistant *Staphylococcus aureus* (MRSA). This type of bacteria causes *staph* infections that are resistant to treatment with usual antibiotics. MRSA has evolved an ability to survive treatment with a variety of beta-lactamase antibiotics, including methicillin, dicloxacillin, nafcillin, and oxacillin.

Therefore, there is a need for improved methods and compositions to treat such antibiotic-resistant strains of microorganisms.

SUMMARY OF THE INVENTION

The present invention relates to a method for treating antibiotic resistant wound infection that includes providing an antimicrobial paste that includes a reaction product of sucralfate with an acid component to form a reaction product, and applying the antimicrobial paste topically to the wound to inhibit the growth of the at least one type of antibiotic resistant microorganism associated with a wound. The reaction product is present in an amount sufficient to at least inhibit the growth of the at least one type of antibiotic resistant microorganism.

The present invention also relates to a method for preventing antibiotic resistant wound infection that includes providing an antimicrobial paste that includes reacting sucralfate and an acid component, and applying the antimicrobial paste topically to a wound to inhibit or avoid the presence or growth of antibiotic resistant microorganisms. The reaction product is preferably present in an amount sufficient to prevent infection of a wound by one or more types of antibiotic resistant microorganisms.

In one embodiment, the reacting is incompletely reacting the sucralfate with the acid component. The wounds to which the compositions are adapted and configured to treat are typically oral, topical, nasal, alimentary, vaginal, ophthalmic, or a combination thereof.

In another embodiment, the acid component is selected to include hydrochloric, hydroiodic, phosphoric, sulfuric, chromic, sulfonic, acetic, citric, ascorbic, or nitric acid, or a combination thereof. Preferably, the reacting occurs no more than about 28 days before applying. The antimicrobial paste optionally may be applied to the wound in association with at least a secondary dressing, occlusive or semi-occlusive dressing, hydrophilic dressing, or a combination thereof. Usually, the antibiotic resistant microorganisms include one or more types of bacteria, one or more types of fungi, or a combination thereof. The antibiotic resistant microorganisms are preferably selected to include bacteria comprising methicillin-resistant *Staphylococcus aureus* or vancomycin-resistant *enterococcus*, or a combination thereof. The antimicrobial paste is generally applied at least once weekly. Furthermore, to inhibit the paste from overdrying, the method preferably also includes covering the applied paste with a second, different cream, ointment, hydrogel, or paste in an amount sufficient to maintain or inhibit loss of moisture from the paste.

The present invention also relates to an antimicrobial sucralfate composition that includes an antimicrobial paste and a supernatant component formed from a reaction product of sucralfate with an acid component. The reaction product is present in an amount sufficient to at least inhibit the growth of at least one type of antibiotic resistant microorganism. The viscosity of the antimicrobial paste is typically from about 50 cP to 350,000 cP.

The antimicrobial paste may advantageously further include a pharmaceutically acceptable carrier that includes one or more of an ointment- or cream-forming agent, and a gel component. The composition preferably further includes a local anesthetic, an additional anti-infective agent, or a combination thereof. The local anesthetic, when present, preferably includes, without limitation, anesthetics of the amide type such as lidocaine, mepivicaine, prilocalne, procaine, or tetracaine, or a combination thereof. The additional anti-infective agent includes, for example, a source of iodide ion, silver, or a combination thereof. In an exemplary embodiment, the composition is substantially stable.

The present invention further relates to an antimicrobial sucralfate composition that includes an antimicrobial paste formed from a reaction product of sucralfate with an acid component, and a moisturizing component to inhibit drying of the antimicrobial paste. The reaction product is present in an amount sufficient to at least inhibit the growth of antibiotic resistant microorganisms.

In a preferred embodiment, the moisturizing component includes methylcellulose, petrolatum, mineral oil, ceresin, lanolin alcohol, mineral wax, povidone or a combination thereof. In another embodiment, the composition further includes a supernatant that is present in the reaction product due to an excess of the sucralfate relative to the acid component.

In addition, the present invention relates to an antimicrobial wound dressing that includes an antimicrobial paste formed from a reaction product of sucralfate incompletely reacted with an acid component, and an absorbent, flexible material that is associated with the antimicrobial paste and provides a substrate to facilitate retention a substantial portion of the antimicrobial paste in association therewith.

The antimicrobial paste is preferably packaged in one or more ointment jars, or syringes or tubes associated with the absorbent, flexible material. In one embodiment, the dressing further includes a backing layer that includes a pressure-sensitive adhesive adapted for contact with the skin or mucosa on one surface thereof. The backing layer is typically disposed adjacent the absorbent, flexible material.

In another embodiment, the adhesive is disposed over a first side of the absorbent, flexible material that includes the antimicrobial paste adapted for application to a wound. Preferably, the acid component includes hydrochloric acid.

The present invention further relates to a method of preparing a stable sucralfate composition that includes providing a source of sucralfate, reacting the sucralfate with an acid component to form a stable composition that includes a paste and a supernatant, and
modifying the supernatant to increase the pH of the supernatant to about 3 or higher. In one embodiment, the acid component reacted exceeds 8 millimoles per 5 grams of sucralfate. In a preferred embodiment, the acid component reacted exceeds 10 millimoles per 5 g of sucralfate but is less than about 55 millimoles per 5 g of sucralfate.

In one embodiment, the molar ratio of the sucralfate to the acid component is about 1:2 to 1:10. Preferably, the molar ratio of the sucralfate to the acid component is about 1:5 to 1:10. In another embodiment, the modifying includes allowing the paste to remain in contact with the supernatant for at least about 18 hours, adding a base to the supernatant, adding supernatant with a pH of greater than about 3, or a combination thereof.

Lastly, the present invention relates to a stable sucralfate composition that includes a reaction product of sucralfate with an acid component. The molar ratio of the sucralfate to the acid component reacted is at least about 1:5 to ensure a sufficient amount of the acid component, but contains an insufficient amount of the acid component to completely dissolve the sucralfate therein. Preferably, the molar ratio of the sucralfate to the acid component is about 1:6 to 1:10.

DETAILED DESCRIPTION OF THE PREFERRED EMBODIMENTS

The present invention relates to the use of sucralfate paste for preventing or treating infection by antibiotic resistant bacteria or fungi, particularly in topical wounds, and specifically *Pseudomonas auruginosa, Escherichia coli*, methicillin-resistant *Staphylococcus aureus* (MRSA) and vancomycin-resistant *enterococcus*. The reaction of sucralfate with an acid component under controlled conditions before dosing limits the reaction to, preferably, an incomplete stage to yield a paste that is biologically activated and advantageous for the treatment of wounds. Preferably, the reaction is limited by the amount of acid with an excess of sucralfate.

The antimicrobial action of sucralfate paste has advantageously been found to have utility for the treatment or prevention of wound infection from a variety of pathogenic organisms, which are preferably antibiotic resistant, including MRSA. The sucralfate paste prepared and used according to the invention has been validated and tested, as described herein, through routine microbial preservative effectiveness research. The testing revealed a surprising and an unexpected antimicrobial effect of the sucralfate paste. Without being bound by theory, it is believed that unreacted sucralfate material, when present, regresses, inhibits, or even prevents the growth of antibiotic-resistant microorganisms, but the potency is believed to be greater with the sucralfate paste prepared by reaction of sucralfate with an acid component, preferably so that the reaction is incomplete and the sucralfate is not completely dissolved. This surprising and unexpected finding suggests for the first time the advantage for treatment or prevention of wound infections from a variety of organisms including the antibiotic resistant organism MRSA, to be achieved by administration of sucralfate paste formed by the reaction of sucralfate with an acid component, preferably the incomplete reaction thereof. Moreover, the inventive sucralfate paste produced substantial reduction in testing of greater than about 4 log reduction in the original inoculums of *Pseudomonas auruginosa, Escherichia coli*, and *Staphylococcus aureus*, and methicillin-resistant *Staphylococcus aureus* (MRSA) as described herein and about 2 log reduction in the original inoculum of *Candida albicans*. The present invention provides a sucralfate composition for the treatment of wounds, and a method for preparation of a sucralfate paste, not only to produce protective and healing benefits, but to treat or prevent wound infection and to otherwise prevent or treat infection particularly by antibiotic resistant microorganisms.

The sucralfate paste of the present invention is preferably an amorphous hydrogel paste preferably formed by the controlled reaction of sucralfate with a limited quantity of an acid component. Although any suitable acid component may be used as described herein, preferably hydrochloric acid (HCl) is used. This compounding process is preferably executed by a pharmacist, dentist, physician, podiatrist, veterinarian, other licensed prescriber or others trained to handle pharmaceutical acids.

The formation of a paste, preferably by the controlled and limited reaction of sucralfate with acid, prior to dosing creates the opportunity to use sucralfate as a physical wound dressing in conditions other than duodenal ulcer. Preferably, the sucralfate and an acid component are reacted no more than about 28 days before application. The sucralfate paste is typically compounded shortly before dispensing to the patient by reacting sucralfate tablets with a volume of acid component, for example, 1.0N HCl, sufficient to initiate paste formation but, in one embodiment, insufficient to cause complete sucralfate dissolution. The tablets can be whole, but are preferably crushed, cut, ground up, milled, or otherwise pulverized to facilitate the reaction. Although a wide variety of pH ranges may be suitable, typically the paste pH is about 2 to 5, more preferably about 3 to 3.8. In an exemplary embodiment, the paste formed in this manner is self-buffered to a pH of about 3.5.

The acid component used to react with the sucralfate can include any suitable acid or acid mixture that reacts with sucralfate to form a paste. For example, the acid component may include hydrochloric, hydroiodic, phosphoric, sulfuric, chromic, sulfonic, acetic, citric, ascorbic, nitric acid, or a combination thereof. Hydrochloric acid is preferred, because of certain drug development conveniences, but alternatives also should provide equivalent therapeutic activity.

HCl has a greater density of proton donation per acid mass than most alternatives for other acids. The paste formed by reaction of sucralfate with HCl is also the most closely related to that formed by reaction with sucralfate and stomach acid, and this most closely characterizes the bulk of wound healing data for sucralfate as used in the treatment of ulcers. The documentation of potential environmental impact of commercial introduction of the anion into commercial distribution for this paste is most readily established with HCl versus other acids. Among acids, HCl offers freedom from taste, smell, tissue staining, and potential toxicity concerns associated with a variety of other acids. For these reasons, HCl is a preferred acid in the acid component.

Other acids may provide additional functions. For example, hydroiodic acid may provide other antimicrobial effect by the donation of the iodide ion. Phosphoric acid, hydroiodic acid, and the weak acids in general can offer the advantages of an integrated acid donor such that paste formation can be executed by simply adding water.

A sufficient amount of the acid component should be reacted with the sucralfate to produce sucralfate polymerization, while, in one embodiment, preferably restricting the total acid availability so as to inhibit or prevent complete dissolution of the sucralfate. The molar ratio of sucralfate and acid component reacted can typically be about 1:0.5 to 1:10, preferably about 1:0.75 to 1:8, and in a more preferred embodiment, about 1:1 to 1:5. A typical ratio used is about 1:1.5. These pastes provide an optimal viscosity and supernatant pH immediately after mixing, but stiffen over the course of 24 hours. In an exemplary embodiment, about 5 grams of sucralfate tablet matrix is reacted with about 2 to 8 millimoles of HCl at a concentration of greater than or equal to 0.1N. Smaller volumes of more concentrated acid may be used. A preferred embodiment uses small volumes of 1.0N HCl. Further, greater quantities of sucralfate and HCl can be employed to produce larger quantities of paste. The amount of the acid component used is based on the feedstock concentration used and the desired thickness of the paste. A larger amount of the acid component tends to produce a thinner paste, while smaller amount produce thicker paste.

Stabilization of the paste for periods of greater than 24 hours has unexpectedly been found to be associated with the use of about 150 percent to 350 percent, of the amount of the acid component previously recognized as the upper limit for the preparation of suitable pastes. Use of more than 8 mL 1.0N HCl per 5 gram sucralfate resulted in too thin a paste and a noticeable drop of supernatant pH below 2. Increasing the molar ratio of sucralfate:acid component to at least about 1:5, preferably about 1:6 to 1:10, produces a paste that is thinner, but suitable (with about 10 percent additional moisture retained within the matrix). Surprisingly and unexpectedly, this paste demonstrates a prolonged stability exceeding 7 days, and preferably exceeding 28 days. As used herein, "substantially stable" or "stable" is defined to mean suitable for use in the present methods for at least 24 hours, preferably for at least 7 days, and more preferably, exceeding 28 days.

In one aspect of the invention, the antimicrobial paste can be applied to the wound with at least a secondary dressing. The secondary dressing can keep the paste over and associated with the wound and help prevent the paste from drying out. The secondary dressing may also act to absorb exudates from the wound, and can be changed periodically typically without disturbing the wound. A suitable secondary dressing may include gauze or cotton.

In another aspect of the invention, a second, different paste, cream, ointment, or hydrogel can be used in combination with the paste or to cover the applied paste to help prevent the paste from drying out. The second, different paste, cream, ointment, or hydrogel is typically spread over the applied paste in an amount sufficient to cover the applied paste partially or completely to inhibit or prevent desiccation of the applied paste. For example, the second, different paste, cream, ointment, or hydrogel can be applied to a wound dressing, which can help retain the sucralfate paste in association with a wound. Suitable agents can include one or more of petrolatum or mineral oil alone, petrolatum and/or mineral oil mixed with lipophilic compounds such as mineral wax, wool wax alcohol, or povidone, or any variety of other pastes or creams or hydrogels. Any suitable amount of such a second, different paste, cream, ointment, or hydrogel may be used in association with the sucralfate paste of the invention, preferably an amount sufficient to minimize or prevent substantially all, or all, moisture loss from the sucralfate compositions of the invention. For example, the second, different paste, cream, ointment, or hydrogel can be applied to create a substantially surrounding barrier, or preferably a complete barrier, between the ambient atmosphere and the sucralfate composition.

The present invention also relates to an antimicrobial sucralfate composition that includes an antimicrobial paste formed from a reaction product of sucralfate with an acid component, and a supernatant formed by the reaction of the sucralfate and the acid component. The reaction of the sucralfate and acid component forms a supernatant that may be decanted or preferably may be retained in whole or in part in association with the paste. Without being bound by theory, keeping the supernatant or other humectant component (e.g., distilled water) associated with the paste can help prevent desiccation and can help increase shelf life.

The viscosity of the sucralfate paste can be adjusted by the amount of acid used to form the paste. Increasing the amount of acid tends to produce a thinner paste. The viscosity of the paste typically can range from about 50 cP to 350,000 cP. The viscosity should be sufficiently low to allow easy spreading of the paste onto the wound but sufficiently high to allow separation of paste from supernatant. Exemplary viscosities might be that of toothpaste, fresh caulk, or rubber cement before curing, but would preferably be that of syrup.

The sucralfate paste preferably is applied directly to a wound with as little dilution as possible by incorporation of other pharmaceutically acceptable carriers. However, it is not beyond the spirit and scope of the invention to formulate the paste to include a pharmaceutically acceptable carrier that includes one or more of an ointment- or cream-forming agent, a gel component, a stabilizing agent, and a humectant component. The paste, with or without associated supernatant is preferably applied directly to the wound with less than 60 percent dilution by other carriers such as ointment, cream or gel forming agents. Placing the pastes into other agents like petrolatum, Aquaphor™, or carboxymethylcellulose provides two to three days of usability, but often reduces the acceptability for use on oral lesions or wet mucosa like vaginal lesions.

A suitable ointment or cream forming agent can include petrolatum, lanolin, polyethylene glycol, mineral oil, mineral wax or a combination thereof. When included in the composition of the invention, the ointment or cream-forming agent is preferably present in an amount sufficient to help retain moisture in the paste to facilitate application. Preferably, the ointment or cream-forming agent also acts to moisturize the wounded membrane, e.g., skin Typical amounts of the ointment or cream-forming agent, when present, are about 10 to 60 weight percent of the total composition, preferably about 15 to 50 weight percent of the total composition, and more preferably, about 25 to 40 weight percent of the total composition.

A suitable gel component to help provide a semisolid matrix can include acacia, alginic acid, bentonite, carbomer, carboxymethylcellulose sodium, cetostearyl alcohol, colloidal silicon dioxide, ethylcellulose, gelatin, guar gum, hydroxyethylcellulose, hydroxypropylcellulose, hydroxypropylcellulose, hydroxylpropylmethylcellulose, magnesium aluminum silicate, maltodextrin, methylcellulose, polyvinyl alcohol, povidone, propylene carbonate, propylene glycol alginate, sodium alginate, sodium starch glycolate, starch, tragacanth, xanthan gum, or a combination thereof. When included in the composition of the invention, the gel component is preferably present in an amount sufficient to bind the resulting composition together to facilitate application of the composition to the wound. Typical amounts of the gel component, when present, are about 0.5 to 40 weight percent of the total composition, preferably about 3 to 30 weight percent of the total composition, and more preferably, about 20 to 25 weight percent of the total composition. In an exemplary embodiment, 20 to 25 weight percent of povidone is included in the composition.

In another embodiment, the composition can also include a local anesthetic, an additional anti-infective agent, or a combination thereof. The anesthetic, when present, acts to numb pain from the wound, while the additional anti-infective can aid in the inhibition or killing of the bacterial or fungal organisms. Any suitable topical anesthetic may be used, including without limitation benzocaine, lidocaine, chloroprocaine, novocaine, mepivicaine, prilocalne, procaine, tetracaine, or a combination thereof. Use of an anesthetic of the ester type such as benzocaine is less preferable due to acid catalyzed hydrolysis of ester structures. The anesthetic, when present, is included in an amount sufficient to relieve pain when administered to the wound. Suitable amounts of the anesthetic, when present, are typically about 1 to about 25 weight percent of the total composition, preferably about 10 to about 25 weight percent of the total composition, and more preferably about 20 weight percent of the total composition.

Any suitable additional anti-infective agent can be used, and when present may include a source of iodide ion, silver, or a combination thereof. In particular, a source of iodide ion is hydroiodic acid, which may be used to form the sucralfate paste itself. The acid could also provide a secondary benefit through release of the iodide ion. The anti-infective agent, when present, is typically included in an amount sufficient to resist the spread of infection in the wound. Suitable amount of the anti-infective, when present, are about 0.05 to 3 percent available iodine, and preferably, about 0.5 to 1.5 percent available iodine The preferred way to inhibit drying of the antimicrobial sucralfate paste is to apply an occlusive or semi-occlusive dressing over the sucralfate paste after application. The sucralfate paste generally dries out after application. The occlusive or semi-occlusive dressing, when present, can preferably include methylcellulose, petrolatum, mineral oil, ceresin, lanolin alcohol, mineral wax, povidone or any combination thereof, which is applied after first applying undiluted sucralfate paste to the wound site.

Another way to inhibit the drying of the antimicrobial sucralfate paste is to incorporate the supernatant into a hydrophilic dressing, which can preferably include methylcellulose, petrolatum, mineral oil, ceresin, lanolin alcohol, mineral wax, povidone, or any combination thereof, which is applied after first applying undiluted sucralfate paste to the wound site.

Yet another way to use the supernatant with potential therapeutic effect is to apply supernatant without further modification directly to the wound prior to covering the wound with sucralfate paste.

Another aspect of the invention is an antimicrobial wound dressing that includes a sufficient amount of the antimicrobial paste associated with an absorbent, flexible material that provides a substrate to retain at least a substantial portion, and preferably substantially all or all, of the antimicrobial paste. The dressing can facilitate the rapid application of the paste to a wound, can keep the paste in position over the wound, and also can help inhibit moisture loss from the paste. The dressing can also facilitate simple reapplication of additional paste or freshly prepared paste to the wound by providing in onto or over the dressing and then reapplying the dressing to the wound.

Preferably, the dressing can also include a backing layer that includes a pressure-sensitive adhesive including one or more adhesive materials adapted for contact with the wound, such as the skin or mucosa on one surface. The backing layer is preferably disposed adjacent the absorbent, flexible material to help retain the dressing in association with the wound, which can include a region adjacent the wound. The adhesive is typically disposed onto the absorbent, flexible material on a side of the material that includes the antimicrobial paste adapted for application to a wound. The adhesive can allow the dressing to be easily attached to the skin or mucosa of the wound, around the wound, or both, while keeping the paste in association with the wound to provide prophylactic or therapeutic effect according to the invention.

A variety of amounts and compositions can be prepared according to the invention. Purely by way of example without limitation, a kit with 2 to 4 grams of sucralfate in a mixture of 5 parts sucralfate with 1 part povidone, about 5 mL purified water and about 2 to 8 millimoles of HCl in a concentration greater than or equal to 0.1N can be provided. The sucralfate can then be reacted with the HCl, preferably in a controlled manner whereby the sucralfate is polymerized, but the complete dissolution of the sucralfate is prevented. Next, the mixture can be triturated into a smooth mass of paste and the resulting paste can be distinguished from and separated from the supernatant to facilitate dosing. The amorphous hydrogel paste can be used to provide complete or partial physical coverage of wounds where gastric acid or local wound bed acidity is not available, or is inconsistently present. A portion of the paste can also be applied to an open oral or topical wound, preferably at least once a week. In other embodiments, the paste can be applied once a day (or more often if needed depending on patient wound dressing requirements), every other day, or twice a week.

One suitable way of preparing the paste is adding about 4 grams of sucralfate to a jar as four 1 gram tablets. About 4 mL of purified water can then be pipetted to wet the sucralfate tablets resulting in tablet pulverization. An amount sufficient to barely cover the tablet could be used. About 5.0 mL 1.0N HCl can subsequently be added to cause paste formation. The paste can be stirred and triturated using a pipette tip. After paste formation, the supernatant can be decanted and retained to allow a small portion to cover the paste after rinsing. The paste can then be washed with distilled water, which can be decanted or allowed to remain over the paste. Finally, the paste can be covered with a small portion of retained supernatant or distilled water. Covering the paste with supernatant or water is not believed to cause significant changes in the paste's characteristics.

Yet another method of preparation involves adding 4 grams of sucralfate to a jar as powder. About 5.5 to 6.0 mL of 1.0N HCl can then be pipetted into the open jar to cause paste formation, preferably after first wetting the powder with purified water in an amount equal or greater than the mass of powder. The reaction takes about a half minute to five minutes. The paste can be stirred and triturated using a pipette tip. After paste formation, the supernatant can be decanted, and supernatant can be retained to allow a small portion to cover the paste after rinsing. The paste can then be rinsed with purified water, and the rinse discarded. The paste can finally be covered with a small portion of retained supernatant or distilled water.

The sucralfate paste is packaged in any suitable container, e.g., 1.5 g of sucralfate paste can be placed in a 5 mL syringe, 4 g of sucralfate paste can be placed in a 15 mL ointment jar, 4 grams of sucralfate paste can be placed in a 5 to 10 gram ointment tube. In a preferred embodiment, the sucralfate paste is retained in a container that inhibits or even prevents moisture from escaping the paste. Without being bound by theory, it is believed that reducing loss of moisture in the paste, which occurs through water migration out of the paste and the package, can aid in preserving the shelf-life and stability of the paste.

In support of preparation of a kit or other product containing the paste compositions of the invention, sucralfate can be repackaged from commercially available 1 gram sucralfate tablets labeled to identify the drug name, the manufacturer contact information and lot number of the sucralfate batch, and an expiration date. Furthermore, 1.0N HCl can be repackaged in 1 to 30 mL quantities in unbreakable plastic tight seal containers, such as vials or dispensing pipettes. These packages can be labeled to reflect the name, strength, and volume of the contents, the manufacturer contact information, lot number, and an expiration date. Packaging and labeling can be constructed to address the requirements for exception to hazardous material shipping regulations as described in 49 C.F.R §173.4. Distilled water can be repackaged in suitable quantities in unbreakable plastic tight seal vials. These packages can be labeled to reflect contents as distilled water, the deliverable volume, the manufacturer contact information, lot number, and expiration date.

Other supplies such as disposable pipettes, stir sticks, oral syringes, ointment jars or tubes, and disposable mixing vessels can be packaged into a kit according to the invention, without relabeling. The final kit, for example, can include the following:

One plastic ointment jar containing four 1 gram sucralfate tablets
One unit dose container of 5 mL water (allowing 4-5 mL to disintegrate tablets and maximize surface area)
One unit dose container of 6 mL of 1.0N HCl
Pipette/stir sticks Another variation of the kit can involve the use of sucralfate raw material rather than commercial tablets. This can be sucralfate active powder, but is preferably an aqueous suspension of sucralfate so that addition of water is not needed.

Another variation of the kit can involve the use of sucralfate volumes sufficient to prepare more than a single dose at a time, such as 100 grams sucralfate with sufficient amounts of ancillary ingredients.

Yet another variation can include a product with the sucralfate and acid components in a two-chambered device. In operation, the trained formulator, or in this case even a consumer, can break or sufficiently remove an internal barrier between the two chambers to initiate reaction, squeeze the reaction product into a jar, mix the product until a paste is formed, and apply the paste directly onto the wound or on a bandage that can be applied as desired to an infection.

In a preferred variation, the process includes reacting the sucralfate and acid component more than 24 hours prior to use to impart prolonged stability of the paste beyond 24 hours after preparation. This method involves the use of a significantly greater excess of acid component relative to sucralfate such that the initial product of the reaction demonstrates a supernatant pH and viscosity characteristics previously considered unsuitable. When the proportion of acid per sucralfate exceeds 8 millimoles per 5 gram, the initial supernatant pH falls to very acidic levels below a pH of 3, and the initial viscosity is too thin to allow adequate separation of paste from supernatant. The pH of the supernatant, however, continues to climb such that a pH of 3 or higher is achieved by 24 hours after the initial reaction, and the viscosity of the paste becomes optimal for use.

For example, a 2 gram mass of sucralfate tablets was disintegrated with about 5 mL purified water prior to reaction with 6 mL 1.0N HCl. In contrast to pastes formed by the reaction of 4 gram mass of sucralfate tablets disintegrated with about 5 mL purified water prior to reaction with 6 mL 1.0N HCl, this paste appeared initially to be too thin, and the supernatant demonstrated a pH of approximately 0.5, which is considered too acidic for safe skin contact. Over a 24 hour period, however, the supernatant demonstrated an increase of pH to achieve a pH of 3.0 to 3.5. The moisture content of the formed paste was about 8 to 10 percent higher than the paste formed with more sucralfate. The viscosity of the paste formed by this novel technique did not demonstrate an unsuitable increase even when observed for periods exceeding 7 days. This variation may be suitable either for preparation in small batches or for manufacture of large batches of paste distributed in ready to use ointment tubes or other suitable containers.

Although a preferred way to provide a stable sucralfate paste is to age the paste with the acidic supernatant, other possibilities are encompassed within the invention. One other possibility for forming stable sucralfate-containing compositions, products, and even wound dressings according to the invention is, after formation of the paste and supernatant, to add base to the supernatant until the appropriate pH is reached. Yet another way to prepare a suitable stable paste is to add previously prepared supernatant that is already at a pH greater than 3, e.g., 3.5-3.8, in an amount sufficient to increase the average pH of all the supernatant above about a pH of 3. In another embodiment, after reaction with excess acid, the supernatant and paste could be separated, such as by centrifuge. The paste could then be directly packaged and aged in its container without the supernatant. Without wishing to be bound by theory, it is believed that stable pastes have at least about 5 percent, typically at least about 10 percent additional moisture retained within the paste in a matrix, compared to a paste that is formed with lower molar ratios of sucralfate: acid component of about 1:3 or lower.

The ratio of sucralfate to acid component reacted is therefore typically at least about 1:5, preferably about 1:6 to 1:10, for reactants that are essentially free of buffering agents. It should be understood that "at least" in this context refers to the amount of acid component. Preferably, the acid component is present in an amount insufficient to completely dissolve the sucralfate therein. For those sucralfate-containing reactants that include a buffering agent, more of the acid component will need to be added to reach an acidic pH below 3, e.g., a pH of about 0.5 to 2.5. The examples herein were prepared using Carafate® sucralfate product. However, without being bound by theory, it is believed that other suppliers of sucralfate such as BK Giulini provide sucralfate that is buffered differently and may tend to require a different amount of acid to achieve a comparable effect. The appropriate amount of acid component can be selected by one of ordinary skill in the art based on the guidance provided herein.

The term "an amount sufficient," as used herein, is encompassed by the dosage amounts and dose frequency schedule described herein, particularly when coupled with prevention or treatment of one or more bacterial strains, especially an antibiotic resistant bacterial strain.

The term "preventing," as used herein, refers to partially or completely preventing or inhibiting formation or growth of bacteria in a subject that may be predisposed to infection but has not yet been exposed to it or been diagnosed as having it. The term "treating," as used herein, refers to partially or completely reducing or eliminating existing colonies of bacteria in a subject, whether before or after its development afflicts a patient. Each of preventing and treating include managing a particular bacterial challenge, particularly antibiotic resistant bacterial infection in a subject, typically a mammal, as well as any beneficial modification of candidate status or the course of infection or any symptoms thereof. The managing may address some or all of the symptoms thereof with or without actually affecting the underlying infection or any disease or condition resulting therefrom.

As used herein, "mammal" is meant the class of warm-blooded vertebrate animals that have, in the female, milk-secreting organs for feeding the young. Mammals include without limitation humans, apes, many four-legged animals, whales, dolphins, and bats. A human is a preferred mammal for purposes of the invention.

As used herein, "wound" refers to any injury to the barrier separating a subject from the environment, for example, skin, mucosa, or other soft tissue that typically acts to inhibit or prevent infection in the subject. The wound may for example, without limitation, occur in an oral, topical, nasal, alimentary, vaginal, or ophthalmic region of a subject, or a combination thereof. A typical type of injury may include, without limitation, a cut, tear, pierce, stab, puncture, abrasion, burn, fissure, incision, or other damage to the barrier that renders the wound susceptible to, or actually associated with, pathogenic infection, such as bacterial or fungal infection. Exemplary wounds might include a post-surgery incision, a cut in the nasal mucosa, abrasions from gravel, or the like.

As used herein, the term "substantially free" or "essentially free" means that a composition contains less than about 10 weight percent, preferably less than about 5 weight percent, and more preferably less than about 1 weight percent of a compound. In a preferred embodiment, these terms refer to less than about 0.5 weight percent, more preferably less than about 0.1 weight percent.

The term "about," as used herein, should generally be understood to refer to both numbers in a range of numerals. For example, "about 1 to 2" should be understood as "about 1 to about 2." Moreover, all numerical ranges herein should be understood to include each whole integer within the range.

Each of the patent applications, patents, publications, and other published documents mentioned or referred to in the Detailed Description is incorporated herein in its entirety by express reference thereto, to the same extent as if each individual patent application, patent, publication, and other published document was specifically and individually indicated to be incorporated by reference.

EXAMPLES

The invention is further defined by reference to the following examples, describing in detail the study used to investigate the compositions and methods of prevention and treatment of the present invention. These examples are for illustrative purposes only, and are not to be construed as limiting the appended claims.

Example 1

Testing of *P. Aeruginosa*, *S. Aureus*, *C. Albicans*, and *A. Niger*

Procedure

Four sets of samples were prepared. The first two sets of samples were used to confirm that sucralfate tablets used in subsequent experiments did not exceed the low bioburden specifications associated with the monograph for EP Microbial Limits Testing. After initial validation of the test method, these test results demonstrated that unreacted sucralfate tablets satisfied the requirements for less than 10 CFU/g total aerobic organisms, less than 10 CFU/g yeast-mold count, and negative growth for *Salmonella*, *E. coli*, *S. aureus* and *P. aeruginosa*/1 g. The third and fourth sets were used to validate the test method and apply the EP and USP test methods for antimicrobial effectiveness testing using sucralfate paste according to the invention.

A container of 4 gram sucralfate tablets was opened, and 4 mL of water was added. The tablets were allowed to disintegrate by adsorption of water. A volume of 6.0 mL 1.0N HCl was transferred into an open jar after disintegration of the tablets with 4 mL purified water. This initiated the paste formation reaction. A half minute to five minutes for reaction was allowed. The sucralfate paste was stirred and triturated using a pipette tip. After paste formation, the supernatant was retained and not diluted further. Without being bound by theory, it is believed that failure to cover the paste with supernatant, an aqueous component (e.g., distilled, deionized, or sterilized water), or another moisture retaining component, can increase drying, and typically can minimize efficacy of the antimicrobial paste. Individual aliquots of paste prepared in this manner weighed 14.8 grams (4.8 grams tablet mass, 4 g purified water and 6 mL HCl 1.0N).

For the fourth set, (paste formed by HCl reaction), each container was inoculated with a suspension of one of the pathogenic test organisms to give an inoculum in compliance with the stated grams of preparation. For the third and fourth sets (reacted with HCl) the system weight was 14.8 grams, made of 4.8 grams total tablet weight, plus 10 grams added fluid weight (4 mL water and 6 mL HCl).

For antimicrobial effectiveness testing, individual containers of 14.8 grams of the test samples of the fourth set were each inoculated to achieve a sample inoculum level of $1\times10^5$ to $1\times10^6$ colony forming units (CFU) per gram by introducing the inoculum into the paste beneath the supernatant and then stirring the paste and supernatant together to distribute the inoculum. The count of viable microorganisms per mL and the volume of each inoculum was recorded accurately. The container was left upright and over time the supernatant separated, restoring its covering position above the paste. The antimicrobial efficacy in terms of absolute inhibition of recovery or log reduction relative to initial inoculation concentration was observed. The population of the challenge organisms was determined by pour plate method at T=0, 2 days, 7 days, 14 days, and 28 days. The plate counts were performed at a 1:10 dilution using tryptic soy broth modified with Tween® and lecithin as the diluent and tryptic soy and Sabouraud dextrose agars, as determined by the plate count validation.

The results are described below.

Results

Validation studies confirmed the absence of interference of sucralfate unreacted granule or sucralfate paste with the agar plate count methods when carried over into the agar material in concentrations expected in these studies. Tests of the sucralfate tablets used to prepare pastes confirmed compliance with the compendia specifications for low microbial bioburden. Sucralfate paste prepared as per the invention demonstrated at least 4 log reduction in all bacterial organisms tested, a 2 log reduction in the fungus *Candida*, and a prevention of new growth of *A. niger*.

Initial Plate Count Results

| Aerobic Plate Count CFU/g | Yeast-Mold Count CFU/g |
| --- | --- |
| <10 | <10 |

Inoculation Levels

| Organism | ATCC Number | CFU/g of Sample |
| --- | --- | --- |
| P. aeruginosa | 9027 | $3.4 \times 10^5$ |
| S. aureus | 6538 | $5.8 \times 10^5$ |
| C. albicans | 10231 | $3.8 \times 10^5$ |
| A. niger | 16404 | $3.3 \times 10^5$ |

Plate Counts—CFU/g

| Organism | T = 0 | T = 2 Days | T = 7 Days | T = 14 Days | T = 28 Days |
| --- | --- | --- | --- | --- | --- |
| P. aeruginosa | $3.5 \times 10^3$ | <10 | <10 | <10 | <10 |
| S. aureus | $4.1 \times 10^3$ | <10 | <10 | <10 | <10 |
| C. albicans | $2.9 \times 10^5$ | N/A | N/A | $3.2 \times 10^3$ | 70 |
| A. niger | $3.4 \times 10^5$ | N/A | N/A | $3.0 \times 10^5$ | $7.5 \times 10^5$ |

Log Reduction

| Organism | T = 2 Days | T = 7 Days | T = 14 Days | T = 28 Days |
| --- | --- | --- | --- | --- |
| P. aeruginosa | >4 | >4 | >4 | >4 |
| S. aureus | >4 | >4 | >4 | >4 |
| C. albicans | N/A | N/A | 2 | 4 |
| A. niger | N/A | N/A | NR/NI | NR/NI |

NR = No Reduction;
NI = No Increase

No increase is defined as not more than 0.5 log unit higher than the previous value measured.

Discussion of Results

A test sample meets the EP (Criteria A) specifications for topical products if there is a 2 log reduction at day 2 and a 3 log reduction at day 7 with no increase at day 28. Fungal organisms must demonstrate a 2 log reduction at day 14 with no increase thereafter during the 28 day test period.

A test sample meets the EP (Criteria B) specifications for topical products if there is a 3 log reduction of bacterial organisms at day 14 with no increase at day 28. Fungal organisms must demonstrate a 1 log reduction at day 14 with no increase thereafter during the 28 day test period.

A test sample meets the EP specifications for oral products if there is a 3 log reduction of bacterial organisms at day 14 with no increase at day 28. Fungal organisms must demonstrate a 1 log reduction at day 14 with no increase thereafter during the 28 day test period.

A test sample meets the USP specifications for oral products if there is a 1.0 log reduction of bacterial organisms at day 14 with no increase at day 28. Fungal organisms must demonstrate no increase from the initial inoculum during the 28 day test period.

A test sample meets the USP specification for topical products if there is a 2.0 log reduction of bacterial organisms at day 14 with no increase at day 28. Fungal organisms must demonstrate no increase from the initial inoculum during the 28 day test period.

The tested sample met the USP requirements for the organisms tested (*P. aeruginosa, S. aureus, C. albicans, A. niger*). At day 14, *P. aeruginosa* and *S. aureus* had a greater than 4 log reduction, but *A. niger* did not experience a reduction during the 28 day testing period. As a result, the tested sample did not pass the EP Antimicrobial Preservative Effectiveness Test for topical and oral products, which also requires sufficient activity against *A. niger*.

This data shows that sucralfate demonstrated mixed results varying by strain. Sucralfate paste surprisingly and unexpectedly demonstrated total kill against the bacteria, *P. Aeruginosa* and *S. Aureus*, surprisingly and unexpectedly partial kill against the fungus *Candida*, and no kill against the mold, *A.*

Niger. These results were preceded by a validation test (not included here) that demonstrated that the sucralfate paste when incorporated in dilute amounts into the growth media did not have an inhibitor effect against growth in agar plates. Therefore no growth on the plates in these studies can be interpreted as true kill of organisms in the sample, rather than merely inhibition of growth on the Petri plate.

Example 2

Testing of *Escherichia Coli* and MRSA

Although this test result surprisingly and unexpectedly demonstrated sufficient log kill against *S. aureus, P. aeruginosa* and *C. albicans* to at least meet the EP standard this did not cause sufficient reduction with *A. niger*. The achieved result was noted to have been consistent with success with the USP Antimicrobial Effectiveness Test (EP requires a reduction, while USP requires only no supported growth for *A. niger*). Although USP criteria are satisfied by the previous test results, they are lacking data for effectiveness against *E. coli*, which is required by USP but not by EP. To demonstrate compliance with USP Antimicrobial Effectiveness Test requirements, the test results of Example 1 were supplemented by an Antimicrobial Effectiveness Test using *E. coli* as the inoculate. Samples of the same lot of sucralfate tablets as previously tested were used to prepare pastes according to the invention by reaction with 1.0N HCl.

It is noteworthy that antimicrobial effectiveness against *S. aureus* and *P. aeruginosa* in test Example 1 was prompt and total. Without being bound by theory, it is believed that the mechanism of this effect is not clear but would not be expected to represent a typical antibiotic effect since trans-membrane permeation of sucralfate or its soluble fragments is essentially zero due to molecular size and charge. Indirect effects such as low pH of the sucralfate paste (e.g., pH around 3.8) or physical effects such as those of mucous coats could explain the antimicrobial activity. Pastes according to the invention could be tested for antimicrobial effectiveness against antibiotic resistant organisms such as MRSA. To test for a previously undemonstrated effect against MRSA, the Antimicrobial Effectiveness test protocol was also run with an additional inoculation challenge using MRSA (MRSA ATCC 33592).

Procedure

The same procedure as Example 1 was followed. Validation protocols previously conducted in Example 1 were not repeated.

Results

Initial Plate Count Results

| Aerobic Plate Count CFU/g | Yeast-Mold Count CFU/g |
|---|---|
| <10 | <10 |

Inoculation Levels

| Organism | ATCC Number | CFU/g of Sample |
|---|---|---|
| E. coli | 8739 | $5.4 \times 10^5$ |
| S. aureus (MSRA) | 33592 | $6.7 \times 10^5$ |

Plate Counts—CFU/g

| Organism | T = 0 | T = 2 Days | T = 7 Days | T = 14 Days | T = 28 Days |
|---|---|---|---|---|---|
| E. coli | $2.8 \times 10^5$ | <10 | <10 | <10 | <10 |
| S. aureus (MSRA) | $3.1 \times 10^5$ | <10 | <10 | <10 | <10 |

Log Reduction

| Organism | T = 2 Days | T = 7 Days | T = 14 Days | T = 28 Days |
|---|---|---|---|---|
| E. coli | >4 | >4.0 | >4.0 | >4.0 |
| S. aureus (MRSA) | >4 | >4.0 | >4.0 | >4.0 |

Discussion of Results

A test sample meets the USP specifications for topical products if there is a 2.0 log reduction of bacterial organisms at day 14 (1.0 log for oral preparations) with no increase at day 28. Fungal organisms must demonstrate no increase from the initial inoculum during the 28 day test period.

A test sample meets the EP/BP (Criteria A) specifications for topical products if there is a 2 log reduction of bacterial organisms at day 2 and a 3 log reduction at day 7 with no increase at day 28. Fungal organisms must demonstrate a 2 log reduction at day 14 with no increase thereafter during the 28 day test period.

A test sample meets the EP/BP (Criteria B) specifications for topical products if there is a 3 log reduction of bacterial organisms at day 14 with no increase at day 28. Fungal organisms must demonstrate a 1 log reduction at day 14 with no increase thereafter during the 28 day test period.

A test sample meets the EP/BP specifications for oral products if there is a 3 log reduction of bacterial organisms at day 14 with no increase thereafter during the 28 day test period. Fungal organisms must demonstrate a 1 log reduction at day 14 with no increase thereafter during the 28 day test period.

The tested samples passed the USP Antimicrobial Preservative Effectiveness Test for topical and oral products for *E. coli* and MRSA. The tested samples also passed the EP/BP (Criteria A and B) Antimicrobial Preservative Effectiveness Test for topical and oral products for *E. coli* and MRSA. The results surprisingly and unexpectedly demonstrated no growth or complete kill for both *E. coli* and MRSA.

Example 3

Confirmation and Test of Potency for Bactericidal Effect Against MRSA

Procedure

Eight individual containers of 14.8 g of test samples for each of three configurations were inoculated with *S. aureas* MRSA ATCC 33592 and tested for microbial recovery immediately and 2 days after inoculation. The three test configurations were as follows.

Test Group 1 was conducted on sucralfate tablets (4×1 gm tablets) disintegrated and suspended in 4 mL water and reacted with 6 mL 1.0N HCl. Test Group 2 was conducted on sucralfate tablets (4×1 gm tablets) disintegrated and suspended in 4 mL water and then further diluted by 6 mL water without addition of HCl. Test Group 3 was conducted on 14.8 grams purified water placed in otherwise empty ointment jars equivalent to those used for Groups 1 and 2.

Four concentrations of S. aureas MRSA ATCC 33592 were prepared. The first concentration was prepared to match the concentration specified in the USP <51> monograph for antimicrobial effectiveness testing ($1.7 \times 10^5$ CFU/g). Other inoculates were prepared with 2-fold, 4-fold and 8-fold greater organism concentrations compared to the USP inoculate concentration. Inoculates were introduced into the sucralfate paste after preparation of the paste, with modifications of the process to establish the control conditions for Test Groups 2 and 3.

Test Group 1 was prepared according to the following procedure. A container holding 4 grams of sucralfate tablets was opened. About 4 mL of water was added, and the tablets allowed to disintegrate by adsorption of water. About 6.0 mL of 1.0N HCl was transferred into the open jar to initiate paste formation. The mix was allowed to react for 0.5 to 5 minutes. The sucralfate paste was stirred and triturated using a pipette tip. After paste formation, the supernatant was retained and not diluted further.

Test Group 2 was prepared according to the following procedure. A container holding 4 grams of sucralfate tablets was opened. About 4 mL of water was added, and the tablets allowed to disintegrate by adsorption of water. About 6.0 mL of purified water was added to produce a thinner slurry with no paste formation. The mix was allowed to stand for 0.5 to 5 minutes. The sucralfate slurry was stirred and triturated using a pipette tip. With no paste formation, the supernatant was retained and not diluted further.

Test Group 3 was prepared according to the following procedure. To an empty ointment jar was added 14.8 grams of water. It was not further diluted or combined with anything else.

For all samples of paste formed by HCl reaction, each container was inoculated with a suspension of the MRSA test organism to give an inoculum in compliance with the stated grams of preparation. The count of viable micro-organisms per mL and the volume of each inoculum was recorded accurately. The actual system weight for 4 gram active drug was 4.8 grams total tablet weight, plus 10 grams added fluid weight (4 mL water and 6 mL HCl or 6 mL water).

For antimicrobial effectiveness testing, the paste was inoculated by introducing the inoculum into the paste beneath the supernatant and then stirring the paste and supernatant together to distribute the inoculum. The container was left upright and over time the supernatant separated, restoring its covering position above the paste. For control samples of Test Group 2 and Test Group 3, the inoculate was introduced below the surface of the suspension or water to mimic the technique used for Group 1. The antimicrobial efficacy in terms of absolute inhibition of recovery or log reduction relative to initial inoculation concentration was calculated.

Results

TABLE 1

Example 3

| | | Plate Count CFU/g T = 0 (immediate post inoculation) | | |
|---|---|---|---|---|
| Inoculation Multiple | Inoculation Level CFU/g | Group 1 SCR HCl Paste | Group 2 SCR Suspension | Group 3 Water |
| 1 fold | $1.7 \times 10^5$ | $2.0 \times 10^3$ | $7.0 \times 10^3$ | $170 \times 10^3$ |
| 2 fold | $3.0 \times 10^5$ | $4.7 \times 10^3$ | $120 \times 10^3$ | $310 \times 10^3$ |
| 4 fold | $6.2 \times 10^5$ | $12.0 \times 10^3$ | $280 \times 10^3$ | $630 \times 10^3$ |
| 8 fold | $1.7 \times 10^6$ | $31.0 \times 10^3$ | $490 \times 10^3$ | $950 \times 10^3$ |

Table 1 demonstrates an immediate reduction in viable microbial recovery with both forms of sucralfate as early as minutes after inoculation. This reduction is surprisingly and unexpectedly more pronounced with sucralfate paste than with sucralfate tablets suspended in water.

TABLE 2

Example 3

| | | Plate Count CFU/g (Log Reduction) T = 2 days | | |
|---|---|---|---|---|
| Inoculation Multiple | Inoculation Level CFU/g | Group 1 SCR HCl Paste | Group 2 SCR Suspension | Group 3 Water |
| 1 fold | $1.7 \times 10^5$ | <10 (>4.2) | <10 (>4.2) | $8.2 \times 10^3$ (1.3) |
| 2 fold | $3.0 \times 10^5$ | <10 (>4.5) | 100 (3.5) | $1.5 \times 10^3$ (1.3) |
| 4 fold | $6.2 \times 10^5$ | <10 (>4.8) | 130 (3.7) | $5.6 \times 10^4$ (1.0) |
| 8 fold | $1.7 \times 10^6$ | 120 (4.0) | 170 (3.8) | $1.1 \times 10^5$ (1.0) |

Table 2 demonstrates a slight reduction (1.0 to 1.3 log reduction) in Group 3 (water control) which was thought, without being bound by theory, to represent the effect of nutrient limitation. Both sucralfate groups demonstrated an antimicrobial effect with a higher level of potency demonstrated by the sucralfate paste compared to sucralfate tablets suspended in water. With 2-fold, 4-fold and 8-fold increase in inoculate concentration, residual organisms are recovered from the Group 2 systems (sucralfate tablets suspended in water). Sucralfate paste continues to demonstrate complete suppression of microbial growth at 2-fold and 4-fold increase in inoculate concentration. Only upon 8-fold increase in inoculate concentration does sucralfate paste demonstrate any recoverable growth of MRSA organism. Even at this level of inoculation, sucralfate paste continues to surprisingly and unexpectedly demonstrate at least 4 log kill of MRSA.

Of the three treatment groups, all demonstrated 2-day reduction in organism recovery. The reduction in the water system (negative control) was less than 1.5 log and, without being bound by theory, may represent the effect of limited nutrient concentration. Both sucralfate systems surprisingly and unexpectedly demonstrated in vitro bactericidal effect with the more potent effect demonstrated by sucralfate paste compared to sucralfate alone suspended in water. Both sucralfate paste and sucralfate alone suspended in water surprisingly and unexpectedly demonstrated at least 3 log kill against all levels of inoculate.

Sucralfate suspended in water, however, failed to tolerate successive increases in inoculate concentrations; recoverable organisms were demonstrated with inoculate concentrations as low as 2 times that typically used in antimicrobial effectiveness tests. Sucralfate paste continued to demonstrate recoveries of <10 CFU at 2 and 4 times the inoculate concentration. At 8-fold increase in the inoculate concentration ($1.1 \times 10^6$), sucralfate paste demonstrated the first measurable organism recovery at 120 cfu/g.

The test results support a conclusion that both sucralfate paste and sucralfate particulate suspension surprisingly and unexpectedly demonstrated an antimicrobial effect, but with a greater potency demonstrated by sucralfate paste. The activity demonstrated by sucralfate particulate suspension eliminates the possibility that the mechanism of antimicrobial effect is the simple result of low pH. A contribution of low pH cannot be ruled out as the explanation for the relative increase in potency demonstrated by the paste compared to the granular form, although further testing can clarify this.

Example 4

Stability Testing

Stability of sucralfate pastes formed by reaction of sucralfate with an acid component have remained limited to durations of about 24 hours primarily because of an increase in viscosity and reduction in paste tackiness that develops with the passage of 24 hours or more time. Opportunities to resist these changes in physical characteristics of the sucralfate paste have been explored with incomplete success by the incorporation of sucralfate pastes into humectant systems such as that afforded by petrolatum, mineral oil, mineral wax, and wool wax alcohol, povidone, carboxymethylcellulose or combinations thereof. Although trials of various systems demonstrate the possibility of a modest increase in the period of physical and chemical stability of sucralfate paste, all of these techniques involve significantly changing the paste from that known to accelerate healing of duodenal ulcer by covering of the ulcer base with a hydrogel formed by reaction of sucralfate with minor content of other formulation excipients with stomach acid to one in which the active drug is significantly incorporated into another external matrix. A different method for extending stability while avoiding embedding the activated sucralfate molecule into a matrix that could change the interaction of the paste with the wound bed was pursued without success through multiple trials. After much testing, preparation of pastes using ratios of sucralfate to acid component that were previously observed to produce unsatisfactory characteristics immediately after compounding were surprisingly and unpredictably found to provide satisfactory characteristics if allowed to age at least 18 hours prior to use.

Pastes were prepared to increase the relative excess of acid per sucralfate beyond the limits previously taught while still avoiding complete sucralfate dissolution. In the series of pastes prepared below (Series 08.0723), pastes with 4 sucralfate 1 gram tablets with 5 mL water and 6 mL acid component represent the high end of the practical limit of the sucralfate: acid ratio previously taught (7.5 millimoles acid component per 5 gram sucralfate). In this example, pastes prepared with twice that amount of acid demonstrated the phenomenon previously reported. These pastes appeared to demonstrate too low a viscosity and too acidic a pH of the supernatant. Direct application of these systems to tissue would not be recommended. For reasons that are not understood, neutralization of acid within the supernatant continued such that after 18 hours, the pH was not different from the pastes prepared with the typical formula of 4 tablets with 5 mL water and 6 mL acid. With the passage of time extending through 8 days, the paste specimens prepared with the typical ratio thickened and became unsuitable for use while pastes which were initially unsuitable developed an optimal viscosity.

Example 4
Technique for Prolonged Paste Stability

| Sucralfate 1 gram | Paste Formulation Proportions of Ingredients | | |
|---|---|---|---|
| Tablets | 4 | 3 | 2 |
| Purified Water | 5 mL | 5 mL | 5 mL |
| HCl 1.0 N | 6 mL | 6 mL | 6 mL |
| Acid: SCR ratio millimoles HCl per 5 gram sucralfate | 7.5:5 | 10:5 | 15:5 |
| pH Supernatant Immediately after compounding | 3.2 to 3.5 | 2.3 | 1.7 |
| pH Supernatant 18 hours | 3.2 to 3.5 | 3.2 to 3.5 | 3.2 to 3.5 |
| pH Supernatant 8 days | 3.2 to 3.5 | 3.2 to 3.5 | 3.2 to 3.5 |
| Viscosity Immediately after compounding | Typical Viscosity similar to thick syrup | Adequate, Less apparent paste mass | Too thin. No adherence to pipette/stir stick |
| Viscosity 18 Hours | Typical Thickest | Adequate | Adequate Thinnest |
| Viscosity 8 Days | Inadequaute. Too Thick Not tacky | Not Optimal | Adequate Similar to 4 gm system on Day 1 |

Example 4 teaches for the first time that prolonged stability of sucralfate pastes formed by reaction of sucralfate with acid can be achieved by extending the relative excess of acid per sucralfate beyond those which yield optimal pastes immediately upon completion of the reaction. By aging the paste thus formed, stabilization of the system is achieved and optimal pH and stability are achieved for prolonged periods.

The foregoing outlines features of several embodiments so that those of ordinary skill in the art may better understand the various aspects of the present disclosure describing the invention. Those of ordinary skill in the art should appreciate that they may readily use the present disclosure as a basis for designing or modifying other chemical or pharmaceutical details for carrying out the same purposes and/or achieving the same advantages of the embodiments introduced herein. Those of ordinary skill in the art should also realize that such equivalent details do not depart from the spirit and scope of the present disclosure, and that they may make various changes, substitutions and alterations herein without departing from the spirit and scope of the present disclosure.

What is claimed is:

1. A method of preparing a stable sucralfate composition comprising:
    providing a source of sucralfate;
    reacting the sucralfate with an acid component to form a stable composition comprising a paste and a supernatant, wherein the acid component reacted exceeds 8 millimoles per 5 grams of sucralfate; and
    allowing the paste to remain in contact with the supernatant for at least about 18 hours so as to increase the pH of the supernatant to about 3 or higher.

2. The method of claim 1, wherein the molar ratio of the sucralfate to the acid component is about 1:2 to 1:10.

3. The method of claim 1, further comprising adding a sufficient amount of a basic component to the supernatant, adding supernatant with a pH of greater than about 3, or a combination thereof.

4. The method of claim 1, wherein the reacting is incompletely reacting the sucralfate with the acid component, wherein reacting occurs no more than about 28 days before the applying, or both.

5. The method of claim 1, wherein the acid component is selected to comprise hydrochloric, hydroiodic, phosphoric, sulfuric, chromic, sulfonic, acetic, citric, ascorbic, or nitric acid, or a combination thereof.

* * * * *